United States Patent [19]
Barnett et al.

[11] Patent Number: 5,904,691
[45] Date of Patent: May 18, 1999

[54] TRACKABLE GUIDE BLOCK

[75] Inventors: Gene H. Barnett, Gates Mills, Ohio; Christopher H. Wood, Bellevue, Wash.; Patrick A. Dayton, Monroe Falls, Ohio

[73] Assignees: Picker International, Inc.; The Cleveland Clinic Foundation, both of Cleveland, Ohio

[21] Appl. No.: 08/938,299

[22] Filed: Sep. 26, 1997

Related U.S. Application Data

[60] Provisional application No. 60/027,402, Sep. 30, 1996.
[51] Int. Cl.$^6$ .................................................. A61B 19/00
[52] U.S. Cl. ................................................ 606/130; 606/129
[58] Field of Search .................................. 606/130, 131, 606/132, 133, 134; 128/303 B, 653.1

[56] References Cited

U.S. PATENT DOCUMENTS

| | | |
|---|---|---|
| 4,809,694 | 3/1989 | Ferrara ........................... 128/303 B |
| 4,991,579 | 2/1991 | Allen . |
| 5,230,338 | 7/1993 | Allen et al. . |
| 5,263,956 | 11/1993 | Nobles ................................... 606/130 |
| 5,517,990 | 5/1996 | Kalfas et al. ....................... 128/653.1 |
| 5,649,936 | 7/1997 | Real . |

FOREIGN PATENT DOCUMENTS 0 832 611  4/1998  European Pat. Off. .

*Primary Examiner*—Michael Buiz
*Assistant Examiner*—Vy Quang Bui
*Attorney, Agent, or Firm*—Timothy B. Gurin; John J. Fry; Eugene E. Clair

[57] ABSTRACT

A surgical guide for use with an image guided surgery includes first and second surfaces. At least three signaling devices such as infrared emitters are disposed on the first surface, and a cylindrical mounting boss is disposed on the second surface. A guide aperture is perpendicular to the first and second surfaces and extends between them. The guide aperture is configured to support a surgical tool such as a biopsy needle. A sleeve may be placed in the aperture to support additional tools.

24 Claims, 4 Drawing Sheets

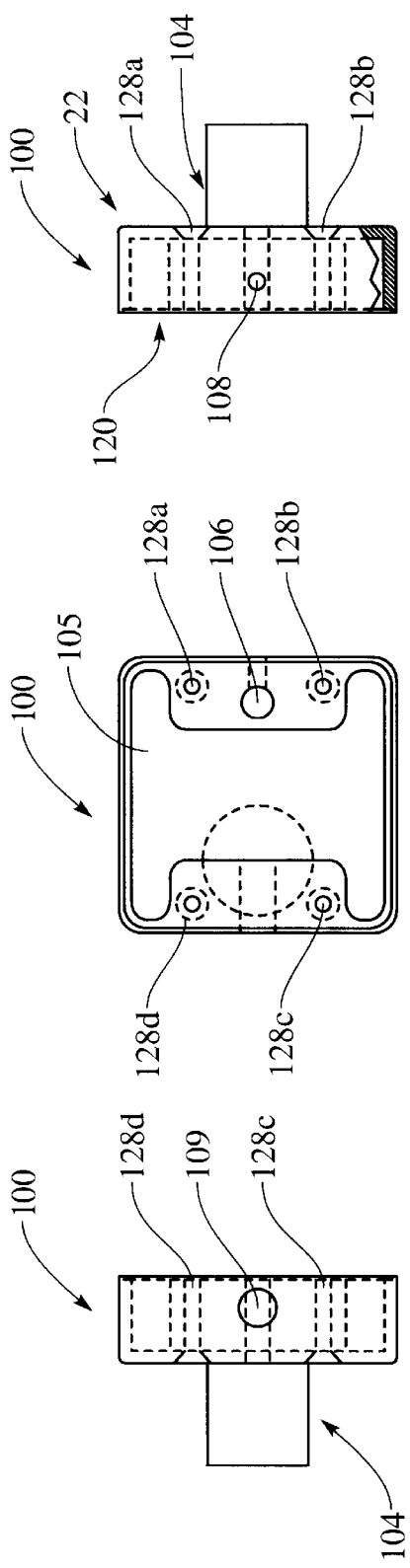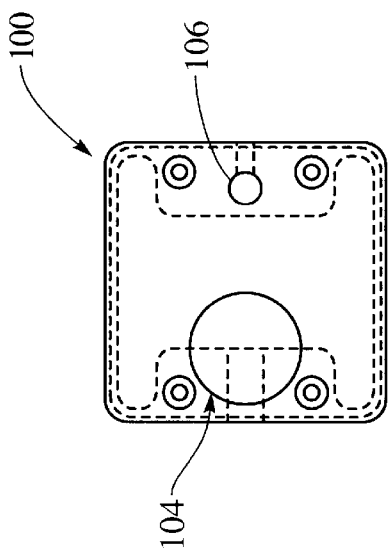

TRACKABLE GUIDE BLOCK

This application is a continuation-in-part of provisional U.S. application Ser. No. 60/027,402 filed Sep. 30, 1996.

BACKGROUND

The present invention relates to the medical diagnostic and surgical arts. It finds particular application in conjunction with neurosurgery and will be described with particular respect thereto. It will be appreciated, however, that the invention finds application in conjunction with biopsies, endoscopic procedures, orthopedic surgeries, other medical procedures, industrial quality control procedures, and the like in which a tool or device must be accurately positioned in relation to an object.

Image guided surgery systems are particularly well adapted to intra-cranial and spinal surgery. These systems use diagnostic images of the patient to assist the physician with presurgical planning and to provide information relating to the position and orientation of the anatomy and instrumentation during a surgical procedure. Image guided surgery systems are a well-suited for use in connection with magnetic resonance ("MR") and computerized tomography ("CT") images, as well as with other imaging modalities.

In cranial applications, a patient reference frame may defined using three or more points fixed in relation to the patient's head. According to one method, at least three markers visible to the imaging device are affixed to the skin prior to imaging. According to another method, anatomical reference points are used. According to a third method, fiducial markers may be affixed to the skull, for example as disclosed in U.S. Pat. No. 4,991,579, Method and Apparatus for Providing Related Images of the Anatomy over time of a Portion of the Anatomy Using Fiducial Implants, to Allen, issued Feb. 12, 1991. Similar techniques may be used to define a patient reference frame with respect to other portions of the anatomy.

An image of the patient having an image reference frame is then obtained. Based on the location of the three or more markers within the image data, the image and patient reference frames can be correlated. Hence, the position of a feature of interest within the image can be determined with respect to the patient reference frame. After image acquisition is complete, the patient can be moved as desired. The patient is subsequently placed in an operating room environment, for example on an operating table.

The patient and operating room reference frames are correlated or "zeroed" by touching the surgical tool to the at least three markers. The position of the tool with respect to the cameras, and hence the position of the markers, is then determined. Inasmuch as the relationship between the patient, operating room, and image frames of reference is known, the position of the tool with respect to the image reference frame can then be determined. Relevant images, with the position of the surgical tool indicated thereon, are then displayed on a monitor. The surgeon is thus provided with a real time indication of the position of the surgical tool with respect to the previously obtained image.

Various surgical procedures require accurate placement of surgical tools in relation to the body. The accurate placement of these devices requires the determination of the trajectory and depth to the intended target. When the trajectory and depth information is determined, it is necessary to preserve that information, and then effectively use it for placement of the surgical device. One potential problem is that the orientation of the surgical device may intentionally or unintentionally change during placement of the device.

Hence, a surgical guide usable in connection with an image guided surgery system and which can be used to accurately place a surgical tool is needed. Such a device should allow the surgeon to readily determine the trajectory and position defined by the guide prior to the insertion of the tool. The guide should be unobtrusive, easy to use, and usable with a variety of surgical tools. Once a desired position has been determined, the guide should also be stable so as to reduce the likelihood of inadvertent changes in position.

SUMMARY

The present invention addresses the above-referenced matters, and others.

According to a first aspect of the invention, an apparatus for guiding a surgical tool includes a first and second major surfaces in spaced relation to each other. The apparatus also includes a guide aperture which intersects the first and second major surfaces. The aperture defines a guide axis and is configured to support the surgical tool along the guide axis. A plurality of position signaling devices having a known relation to the guide axis are adapted for operative communication with an image guided surgery system.

According to a more limited aspect of the invention, at least three position signaling devices are disposed on the first major surface.

According to another more limited aspect of the present invention, the apparatus includes a means such as a boss having a cylindrical exterior surface for attaching the apparatus to an instrument holder. According to a still more limited aspect, the means for attaching is disposed on the second major surface. According to another still more limited aspect of the present invention, the means for attaching defies a longitudinal axis which is parallel to the guide axis.

According to another more limited aspect of the invention, the apparatus includes a sleeve which is insertable within the guide aperture and which is adapted to support a desired surgical tool.

According to another more limited aspect of the invention, the first major surface has at least a first transverse dimension and a distance between the first and second major surfaces which is less than the first transverse dimension.

According to other more limited aspects of the invention, the position signaling devices may be reflective elements or an infrared emitters, the first major surface may be rectangular, circular, or x-shaped, and at least three position signaling devices may be disposed in a plane orthogonal to the guide axis.

According to yet another aspect of the invention, an apparatus for guiding the application of a surgical tool in relation to an object includes an image guided surgery system and a surgical guide. The surgical guide includes means for supporting the surgical tool along a guide axis and three position signaling devices adapted for operative communication with the image guided surgery system. The three position signaling devices are disposed in a plane which does not include the guide axis.

According to a more limited aspect, the plane is orthogonal to the guide axis. According to another more limited aspect, the surgical guide includes a first major surface upon which the three position signaling devices are disposed and a second major surface parallel to the first major surface and perpendicular to the guide axis.

According to yet another more limited aspect of the invention, the means for supporting includes an aperture which intersects the first and second surfaces. According to a still more limited aspect of the invention, the means for supporting includes a sleeve which is insertable in the aperture. The sleeve is configured to support a desired tool.

A first advantage of the present invention is that accurate positioning of a surgical tool is facilitated.

Another advantage of the present invention is that it provides a surgical guide which can be used to guide a variety of surgical tools but which is easy to use and unobtrusive.

Still another advantage of the present invention is that interference between the line of sight and the emitters due to the mounting structure is minimized.

Yet another advantage is it is not necessary to place the surgical guide in physical contact with the patient.

Yet another advantage of the present invention is that attachment to a holding device is facilitated.

Still other advantages will be appreciated by those skilled in the art upon reading and understanding the appended description.

DRAWINGS

FIG. 2a is a top view of a guide block according to the present invention.

FIG. 2b is a bottom view of a guide block according to the present invention.

FIG. 2c is a left side view of a guide block according to the present invention.

FIG. 2d is a right side view of a guide block according to the present invention.

DESCRIPTION

The present invention is preferably operated in conjunction with an image guided surgery system such as disclosed in commonly assigned U.S. Pat. No. 5,517,990, *Stereotaxy Wand and Tool Guide,* to Kalfas, et al. issued May 21, 1996 and expressly incorporated by reference herein. In a preferred application, an infrared localizer is used. The localizer includes two spaced apart infrared cameras, which are located in the operating room and define an operating room reference frame. The cameras are mounted in a generally stationary location, for example on the operating table, on the ceiling or wall, or on a stand.

A surgical tool, guide, or other device for use with the infrared cameras includes at least three infrared emitters having a known relationship to the tip or other feature of the tool. Additional emitters may also be used to permit continued tracking of the device in the event that the line of sight between one or more of the emitters becomes interrupted and to provide increased accuracy. Depending on the characteristics of the localizer, fewer emitters may also be used.

Based on the signals detected by the cameras, the position of the surgical tool or device with respect to the operating room reference frame can be determined. Thus, the localizer system can be used to determine the position of at least one surgical tool.

Figure 1:
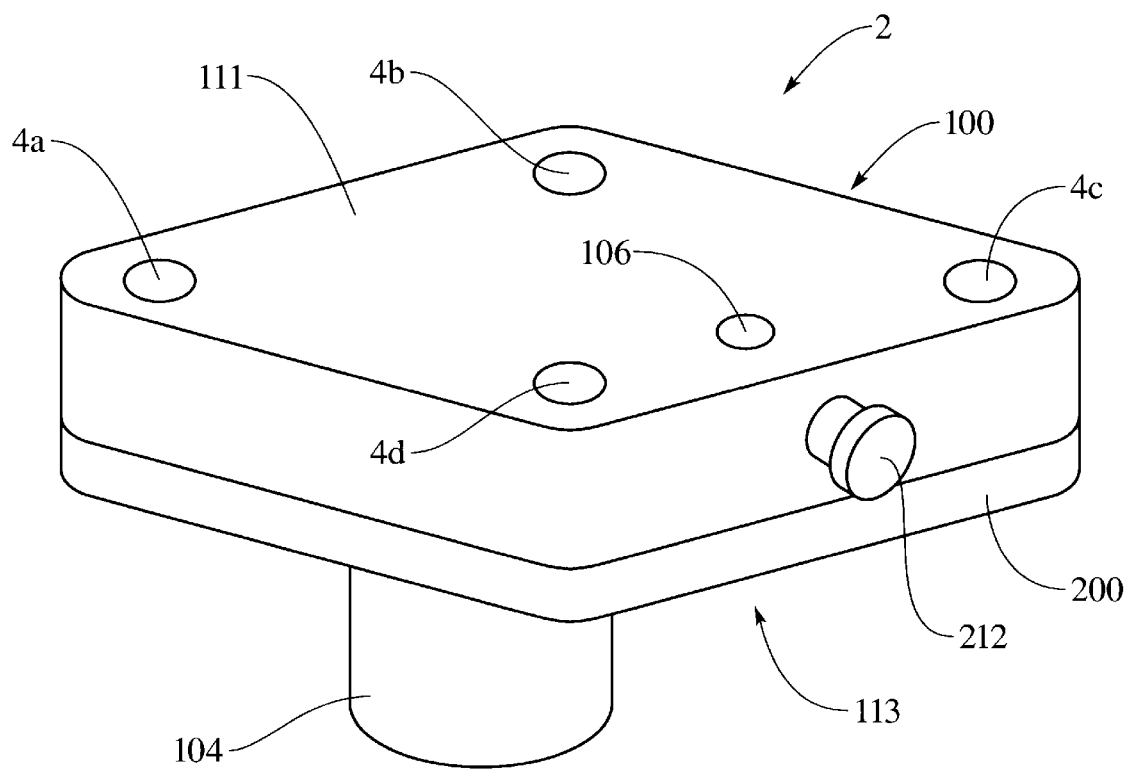
FIG. 1 is a perspective view of a surgical guide according to the present invention.

With reference to FIG. 1, a surgical guide 2 includes position signaling devices such as infrared emitters 4a–4d. While the invention is described for use with an infrared localizer, it will be appreciated that alternate position signaling devices, such as infrared detectors, sonic receivers or transmitters, or reflective elements may be used depending on the requirements of the particular localizer system. In an alternate embodiment, the emitters 4a–4d could be replaced by a rigidly attached mechanical arm capable of recording the position of the block.

The surgical guide also includes a mounting structure such as a boss 104 having a cylindrical exterior. The cylindrical boss 104 is used to attach the surgical guide 2 to an instrument holder. The mounting structure can be located anywhere with respect to the emitters 4a–4d, but should not interfere with the line of sight between the emitters 4a–4d and the detectors. In one embodiment, the a holding device such as a Greenberg clamp is affixed to the cylindrical boss 104. The surgical guide 2 can thus be mounted in a known and selectively variable relationship to an operating table, patient, patient holding device, or other location in the operating room.

A guide structure such as a guide aperture 106 which supports a surgical tool such as a wand, probe, drill, biopsy guide, radiation source, or the like extends from the top 111 to the bottom 113 surface of the surgical guide 2 and is orthogonal with respect to the top and bottom surfaces. The aperture 106 defines a guide axis for guiding the application of the surgical tool. A set screw 212 holds the surgical device in a desired position within the guide aperture 106. The cylindrical boss 104 and the emitters 102a–d are mounted on opposite sides of the guide block 100 to make room for the guide aperture 106 and to reduce the likelihood of the mounting structure interrupting the line of sight between the emitters 4a–4d and the cameras.

Because the location of an axis defined by the guide aperture 106 with respect to the emitters 4a–4d are known, the trajectory of a surgical device inserted in the guide aperture 106 can be continuously determined using the localizer. The surgical guide 2 is characterized prior to use, i.e. the precise positional relationship between the emitters 4a–4d and the other components of the guide 2 (in particular the guide aperture 106) is determined and stored in memory. In a preferred embodiment, the information is stored in programmable memory mounted inside the surgical guide 2. Alternatively, the memory could be located in a connecting cable, digitizer, or computer system.

With references to FIGS. 2a, 2b, and 2c, the surgical guide includes a guide block 100 and a cover 200. The mounting boss 104 is mounted to the bottom surface 113 of the guide block with the longitudinal axis of the boss 104 orthogonal to the bottom surface 113 and parallel to the guide axis. Guide aperture 106 extends from the top surface 120 to the bottom surface 113 of the guide block 100, and an aperture 108 for accepting the set screw 212 extends between an exterior surface of the guide block 100 and the guide aperture 106. Wiring ingress and egress is through the wiring aperture 109.

Figure 3A:
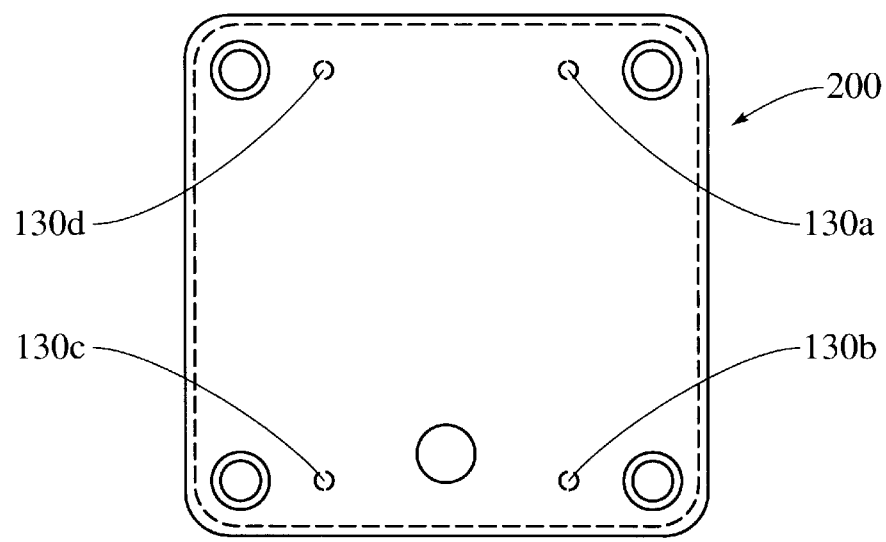
FIG. 3a is a top view of a cover according to the present invention.
Figure 3B:
FIG. 3b is a side view of a cover according to the present invention.
Figure 3C:
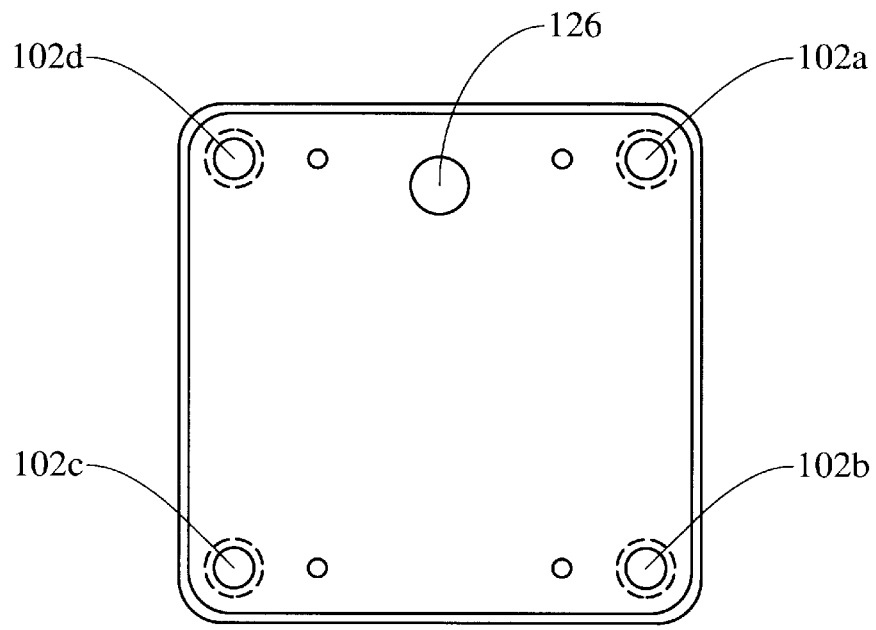
FIG. 3c is a bottom view of a cover according to the present invention.

With reference to FIGS. 3a, 3b, and 3c, the cover 200 includes emitter apertures 102a–102d into which the emitters 4a–4d may be mounted. The cover 200 also includes an aperture 126 which corresponds to the guide aperture 106 and forms a part thereof. The cover 100 mates with the upper surface 120 of the guide block 100 and is fastened thereto using screws which extend through screw holes 128a–128d and engage corresponding blind holes 130a–130d in the cover 200. When installed, the cover 200 forms the upper surface 111 of the surgical guide 2.

The guide block 100 and cover 200 may also take other configurations. In a particularly advantageous alternate configuration which is illustrated in the perspective view of FIG. 1, the cylindrical boss 104 forms part of the cover 200, while the emitter apertures are located on the opposite surface of the guide block 100 so that the emitters 4a–4d are mounted to the guide block 100. Thus, the guide block 100 forms the upper surface 111 of the surgical guide 2 while the cover 200 forms the lower surface 112. Installation of the emitters 4a–4d and routing of wiring is thereby simplified, while the overall configuration of the surgical guide 2 remains unchanged.

In a preferred embodiment, the guide aperture 106 is a cylindrical hole compatible with a common biopsy guide, although it could be of other suitable shape or size. The distance between the upper 111 and lower 113 surfaces of the surgical guide 2 (with the cover 200 installed) is 0.750 inches (1.905 cm), and the guide block is 2.5 inches (6.35 cm) by 2.5 inches (6.35 cm). The guide aperture 106 has a length of 0.750 inches (1.905 cm) and a diameter of 0.270 inches (0.686 cm).

The surgical guide 2 may also be used with surgical tools other than biopsy guides or which require alternate guide dimensions. With reference to FIG. 4, a guide member such as an annular cylindrical sleeve 210 may be inserted into the guide aperture 106 and secured using the set screw 212 inserted in aperture 108. The dimensions of the sleeve 210 are selected to accommodate and provide adequate support for a desired surgical tool. By way of example, the length and internal diameter of the sleeve 210 may be selected to accommodate a particular drill bit. Alternatively, a clamp could be affixed to the surgical tool. The clamp in turn holds the tool during use.

Figure 4A:
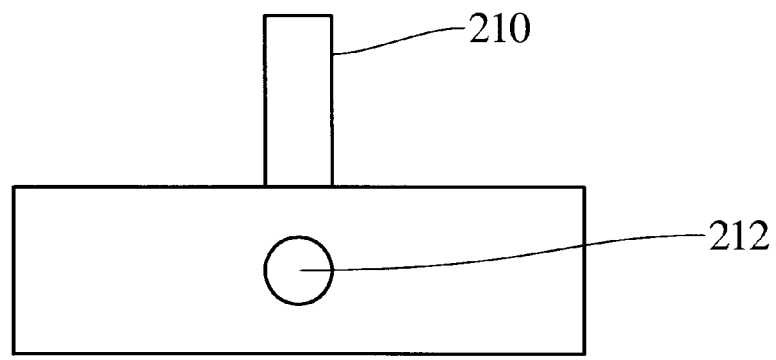
FIG. 4a is a side view of an alternate embodiment of a surgical guide according to the present invention.
Figure 4B:
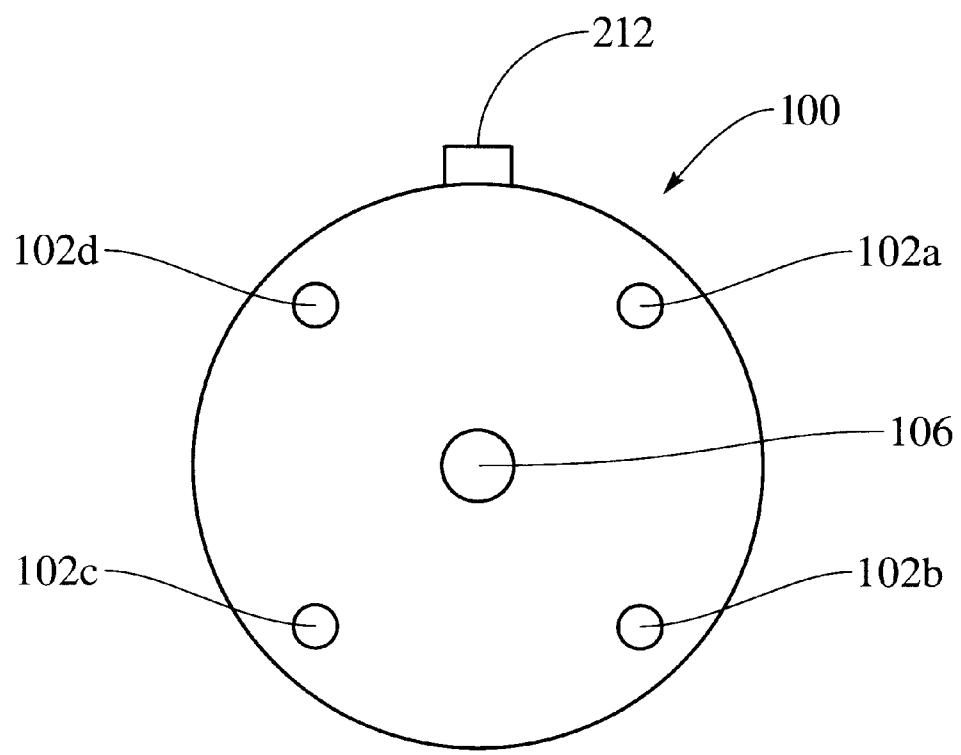
FIG. 4b is a top view of an alternate embodiment of a surgical guide according to the present invention.

While the surgical guide has been described as having a generally block-like shape, other configurations are possible. For example, the emitters may be affixed to an x-shaped or similar structure in which the emitters are maintained in a desired spacing and configuration. With reference to FIG. 4a and 4b, the surgical guide 2 may, rather than being square, take on a disc shape. A particular advantage of such a configuration is that attachment to a Greenberg clamp or other holding device is facilitated. The guide block may also be integrated into the holding device.

To provide a reference surface, the surface 111 of the surgical guide which ordinarily faces the surgeon is preferably planar and orthogonal to the guide axis defined by the guide aperture 106. Alternately, the reference surface may be a target point on the surgical guide, for example a geometrically distinct region such as a small divot or a point marked with a marking such as an "x." Preferably, however, the reference surface is clearly identifiable as such by the surgeon.

The surgeon uses the surgical guide 2 by moving it in relationship to the patient and referring to corresponding images displayed on a computer monitor. The position of the guiding mechanism or aperture 106 is determined by the localizer, and this information is communicated to the surgeon through the concept of a "virtual tip." Thus, the position and trajectory defined by the guide aperture 106 can be calculated and displayed with respect to relevant images of the patient even if a tool is not inserted in the guide aperture 106. The distance along the guide axis to a desired point within the patient may also be computed and displayed.

When the surgical guide 2 has been properly positioned, it is fixed in place. The guide is ordinarily placed close to, but not in physical contact with, the patient. The guide may be placed in such contact, but it is not required to provide adequate support. Once the guide 2 has been fixed in place, the surgical tool can be installed in the guide aperture 106 the requisite surgical procedure performed. Alternately, the tool may first be placed in the guide aperture 106 and the surgical guide 2 adjusted as desired. If the trajectory of the device or the distance required to reach the target changes during the surgical procedure, that information is communicated to the surgeon via the display so that any necessary adjustments may be made. It should be noted that, when used in connection with the surgical guide 2, it is not necessary that the surgical tool be equipped with its own signaling devices.

Inasmuch as the reference surface defines a surface which is orthogonal to the guide axis (or alternately defines a point in a plane orthogonal to the guide axis), the reference surface may be used to determine or verify the distance, along the guide axis, between the reference surface and a target point within the patient. Thus, for example, the surgeon may touch the tip of a tool to the reference surface. The distance between the reference surface and the target point as determined based on the position of the tool may be compared to the position determined based on the position of the surgical guide. A variation in these distances indicates that recalibration of the tool, the surgical guide, or both may be needed.

The invention has been described with reference to the preferred embodiment. Obviously, modifications and alterations will occur to others upon reading an understanding the preceding description. It is intended that the invention be construed as including all such modifications an alterations insofar as they come within the scope of the appended claims or the equivalents thereof.

What is claimed is:

1. An apparatus for guiding the application of a surgical tool in relation to an object, the apparatus comprising:
   a first major surface; and
   a second major surface in spaced relation to the first major surface;
   a guide aperture which intersects the first and second major surfaces, the guide aperture defining a guide axis and being configured to support the surgical tool along the guide axis; and
   a plurality of position signaling devices having a known relationship to the guide axis, the signaling devices being adapted for operative communication with an image guided surgery system.

2. An apparatus according to claim 1 comprising at least three position signaling devices disposed on the first major surface.

3. An apparatus according to claim 2 comprising means disposed at a location offset from the guide axis for attaching the apparatus to a holding device.

4. An apparatus according to claim 3 wherein the means for attaching comprises a boss having a cylindrical exterior surface.

5. An apparatus according to claim 3 wherein the means for attaching is disposed on the second major surface.

6. An apparatus according to claim 5 wherein the means for attaching defines a longitudinal axis and the longitudinal axis is parallel to the guide axis.

7. An apparatus according to claim 1 comprising a sleeve which is insertable within the guide aperture and which is adapted to receive a desired surgical tool.

8. An apparatus according to claim 1 wherein the first major surface has at least a first transverse dimension and a distance between the first and second major surfaces at the location of the guide aperture is less than the first transverse dimension.

9. An apparatus according to claim 1 wherein the position signaling devices comprise one of reflective elements and infrared emitters.

10. An apparatus according to claim 1 wherein the first major surface is one of rectangular, circular and x-shaped.

11. An apparatus according to claim 1 comprising at least three position signaling devices disposed in a plane orthogonal to the guide axis.

12. An apparatus for guiding the application of a surgical tool in relation to an object, the apparatus comprising:
    an image guided surgery system; and
    a surgical guide comprising
        three position signaling devices adapted for operative communication with the image guided surgery system, the three position signaling devices disposed in a plane; and
    means for supporting the surgical tool along a guide axis, which guide axis intersects the plane at a known non-zero angle.

13. An apparatus according to claim 12 wherein the plane is orthogonal to the guide axis.

14. An apparatus according to claim 12 wherein the surgical guide comprises a first major surface and the means for supporting comprises a guide aperture which intersects the first major surface.

15. An apparatus according to claim 14 wherein the three signaling devices are disposed on the first major surface.

16. An apparatus according to claim 14 wherein the surgical guide comprises a second major surface and further comprising a mounting boss disposed on the second major surface.

17. An apparatus according to claim 12 wherein the surgical guide comprises
    a first major surface, the three position signaling devices being disposed thereon;
    a second major surface parallel to the first major surface and perpendicular to the guide axis.

18. An apparatus according to claim 17 wherein the means for supporting comprises an aperture which intersects the first and second surfaces.

19. An apparatus according to claim 13 wherein the means for supporting comprises a sleeve insertable within the aperture, the sleeve being configured to support a desired tool.

20. An apparatus according to claim 12 wherein the surgical guide comprises four signaling devices.

21. An apparatus according to claim 12 comprising means for defining a reference surface.

22. A method for guiding the application of a surgical tool, the method comprising the steps of:
    positioning a surgical guide in relation to a patient, the surgical guide comprising
    a structure configured to support the surgical tool along a guide axis;
    at least three position signaling devices adapted for operative communication with an image guided surgery system and disposed in a plane orthogonal to the guide axis;
    using the image guided surgery system to determine a position of the guide axis; and
    using the surgical guide to support the surgical tool.

23. A method according to claim 22 wherein the structure configured to support the surgical tool comprises an aperture and further comprising the step of inserting within the aperture a member configured to support the surgical tool.

24. A method according to claim 22 wherein the surgical guide comprises a first major surface, a second major surface in spaced relation to the first major surface and parallel thereto, and a mounting structure disposed on the second major surface, the position signaling devices being disposed on the first major surface.

* * * * *